United States Patent
Anderson et al.

(10) Patent No.: US 9,381,071 B2
(45) Date of Patent: Jul. 5, 2016

(54) STRAIGHT 'N' CLEAR THERMOFORMING PLASTIC

(75) Inventors: Michael C. Anderson, Palmetto, FL (US); John F. Bozman, Bradenton, FL (US)

(73) Assignee: DENTSPLY International Inc., York, PA (US)

(*) Notice: Subject to any disclaimer, the term of this patent is extended or adjusted under 35 U.S.C. 154(b) by 616 days.

(21) Appl. No.: 12/709,704

(22) Filed: Feb. 22, 2010

(65) Prior Publication Data

US 2010/0151205 A1 Jun. 17, 2010

Related U.S. Application Data

(63) Continuation of application No. 11/438,160, filed on May 22, 2006, now abandoned, which is a continuation of application No. 11/281,086, filed on Nov. 17, 2005, now abandoned, which is a continuation-in-part of application No. 11/153,794, filed on Jun. 15, 2005, now abandoned.

(60) Provisional application No. 60/628,812, filed on Nov. 17, 2004.

(51) Int. Cl.
| | | |
|---|---|---|
| *B32B 3/00* | (2006.01) |
| *A61C 7/08* | (2006.01) |
| *B29C 51/02* | (2006.01) |
| *A63B 71/08* | (2006.01) |
| *B29C 47/00* | (2006.01) |
| *B29C 51/10* | (2006.01) |
| *B29K 25/00* | (2006.01) |
| *B29K 27/06* | (2006.01) |
| *B29L 31/00* | (2006.01) |

(52) U.S. Cl.
CPC . *A61C 7/08* (2013.01); *B29C 51/02* (2013.01); *A63B 71/085* (2013.01); *B29C 47/0021* (2013.01); *B29C 47/0054* (2013.01); *B29C 47/0057* (2013.01); *B29C 47/0069* (2013.01); *B29C 51/10* (2013.01); *B29C 2791/006* (2013.01); *B29K 2025/00* (2013.01); *B29K 2027/06* (2013.01); *B29K 2995/0029* (2013.01); *B29L 2031/7536* (2013.01); *Y10T 428/24479* (2015.01)

(58) Field of Classification Search
CPC . Y10T 428/24479; A61C 7/08; A63B 71/085
USPC ............... 428/156, 172, 212, 218, 521, 523; 433/6, 18, 24, 213, 223; 128/961, 862
See application file for complete search history.

(56) References Cited

U.S. PATENT DOCUMENTS

| 3,303,844 | A | * | 2/1967 | Johnson et al. | 128/862 |
| 3,528,132 | A | * | 9/1970 | Greenberg et al. | 425/156 |

(Continued)

FOREIGN PATENT DOCUMENTS

| FR | 2 763 238 | 11/1998 |
| WO | WO 06/009745 | 1/2006 |
| WO | WO 06/055700 | 5/2006 |

*Primary Examiner* — Donald J Loney
(74) *Attorney, Agent, or Firm* — David A. Zdurne; Douglas J. Hura; Leana Levin

(57) ABSTRACT

Thermoforming of plastic sheets over a model includes varying the thickness in the area that is stretched over the model so that when it thins it becomes more uniform in thickness. The plastic sheet is fabricated in a substantially uniform thickness but with a preformed a complex profile or 3D area that partially builds in part of the area that would be stretched so that it thins much less than a flat sheet. Combinations of these elements may also be made.

12 Claims, 4 Drawing Sheets

(56) References Cited

U.S. PATENT DOCUMENTS

| | | | |
|---|---|---|---|
| 3,682,571 A | | 8/1972 | Greenberg et al. |
| 4,063,552 A | * | 12/1977 | Going et al. ............... 128/861 |
| 4,482,321 A | * | 11/1984 | Tabor et al. ............... 433/71 |
| 4,672,959 A | * | 6/1987 | May et al. ............... 128/861 |
| 4,751,935 A | | 6/1988 | Mast et al. |
| 4,797,313 A | * | 1/1989 | Stolk et al. ............... 428/156 |
| 5,139,419 A | | 8/1992 | Andreiko et al. |
| 5,368,478 A | | 11/1994 | Andreiko et al. |
| 5,395,238 A | | 3/1995 | Andreiko et al. |
| 5,431,562 A | | 7/1995 | Andreiko et al. |
| 5,447,432 A | | 9/1995 | Andreiko et al. |
| 5,454,717 A | | 10/1995 | Andreiko et al. |
| 5,464,349 A | | 11/1995 | Andreiko et al. |
| 5,474,448 A | | 12/1995 | Andreiko et al. |
| RE35,169 E | | 3/1996 | Lemchen et al. |
| 5,518,397 A | | 5/1996 | Andreiko et al. |
| 5,533,895 A | | 7/1996 | Andreiko et al. |
| 5,562,449 A | * | 10/1996 | Jacobs et al. ............... 433/215 |
| 5,592,951 A | * | 1/1997 | Castagnaro et al. ............... 128/848 |
| 5,609,940 A | * | 3/1997 | Inaba et al. ............... 428/156 |
| 5,683,243 A | | 11/1997 | Andreiko et al. |
| 5,957,689 A | * | 9/1999 | Wagner ............... 433/215 |
| 5,975,893 A | | 11/1999 | Chishti et al. |
| 5,979,449 A | * | 11/1999 | Steer ............... 128/848 |
| 6,015,289 A | | 1/2000 | Andreiko et al. |
| 6,017,217 A | * | 1/2000 | Wittrock ............... 433/37 |
| 6,082,995 A | | 7/2000 | Wise |
| 6,210,162 B1 | | 4/2001 | Chishti et al. |
| 6,217,325 B1 | | 4/2001 | Chishti et al. |
| 6,227,850 B1 | | 5/2001 | Chishti et al. |
| 6,244,861 B1 | | 6/2001 | Andreiko et al. |
| 6,299,440 B1 | | 10/2001 | Phan et al. |
| 6,309,215 B1 | | 10/2001 | Phan et al. |
| 6,318,994 B1 | | 11/2001 | Chishti et al. |
| 6,371,759 B1 | | 4/2002 | Schwartz |
| 6,386,864 B1 | | 5/2002 | Kuo |
| 6,390,812 B1 | | 5/2002 | Chishti et al. |
| 6,394,801 B2 | | 5/2002 | Chishti et al. |
| 6,398,548 B1 | | 6/2002 | Muhammad et al. |
| 6,406,292 B1 | | 6/2002 | Chishti et al. |
| 6,409,504 B1 | | 6/2002 | Jones et al. |
| 6,450,807 B1 | | 9/2002 | Chishti et al. |
| 6,454,565 B2 | | 9/2002 | Phan et al. |
| 6,457,972 B1 | | 10/2002 | Chishti et al. |
| 6,463,344 B1 | | 10/2002 | Pavloskaia et al. |
| 6,471,511 B1 | | 10/2002 | Chishti et al. |
| 6,485,298 B1 | | 11/2002 | Chishti et al. |
| 6,488,499 B1 | | 12/2002 | Miller |
| 6,514,074 B1 | | 2/2003 | Chishti et al. |
| 6,524,101 B1 | | 2/2003 | Phan et al. |
| 6,554,611 B2 | | 4/2003 | Chishti et al. |
| 6,572,372 B1 | | 6/2003 | Phan et al. |
| 6,582,227 B2 | | 6/2003 | Phan et al. |
| 6,602,070 B2 | | 8/2003 | Miller et al. |
| 6,602,076 B2 | | 8/2003 | Adams |
| 6,607,382 B1 | | 8/2003 | Kuo et al. |
| 6,621,491 B1 | | 9/2003 | Baumrind et al. |
| 6,626,666 B2 | | 9/2003 | Chishti et al. |
| 6,629,840 B2 | | 10/2003 | Chishti et al. |
| 6,633,789 B1 | | 10/2003 | Nikolskiy et al. |
| 6,665,570 B2 | | 12/2003 | Pavloskaia et al. |
| 6,682,346 B2 | | 1/2004 | Chishti et al. |
| 6,685,469 B2 | | 2/2004 | Chishti et al. |
| 6,685,470 B2 | | 2/2004 | Chishti et al. |
| 6,688,886 B2 | | 2/2004 | Hughes et al. |
| 6,699,037 B2 | | 3/2004 | Chishti et al. |
| 6,705,861 B2 | | 3/2004 | Chishti et al. |
| 6,705,863 B2 | | 3/2004 | Phan et al. |
| 6,729,876 B2 | | 5/2004 | Chishti et al. |
| 6,832,914 B1 | | 12/2004 | Bonnet et al. |
| 2002/0006597 A1 | | 1/2002 | Andreiko et al. |
| 2004/0038171 A1 | | 2/2004 | Jacobs et al. |
| 2005/0048433 A1 | | 3/2005 | Hilliard |
| 2007/0122591 A1 | | 5/2007 | Anderson et al. |

\* cited by examiner

STRAIGHT 'N' CLEAR THERMOFORMING PLASTIC

RELATED APPLICATIONS

This application is a Continuation of U.S. application Ser. No. 11/438,160 filed on May 22, 2006 (now abandoned), which is a Continuation of U.S. application Ser. No. 11/281,086 filed on Nov. 17, 2005 (now abandoned), which also claims the benefit of U.S. Provisional Application Ser. No. 60/628,812 filed on Nov. 17, 2004; and also claims the benefit of U.S. application Ser. No. 11/153,794 filed on Jun. 15, 2005 (now abandoned), which claims the benefit of U.S. Provisional Application Ser. No. 60/581,119, filed Jun. 18, 2004.

BACKGROUND OF THE INVENTION

Plastic sheets for dental devised have been used for decades. They are heated used an electric grid and then when lowered to the model, a vacuum draws the plastic precisely to the model of the teeth. Indications for use are indirect bonding of orthodontic appliances, orthodontic retainers, mouth guards for sports, and aligners for correcting minor malocclusions. One of the biggest drawbacks is that as that the plastic thins as it is stretched over the plaster model of the teeth causing it to fail quicker, either in occlusion or because of the vacuum force drawing so hard at the outset. This failure can cause hours of extra labor to create a new aligner, as the teeth will have moved since the last impression was taken and the model made, and the doctor or lab must go through the whole process again. Also, it delays the treatment and can lead to relapse if the patient doesn't return immediately. Generally, these sheets are made with a medical grade plastic that severely limits the range of plastic choices. It is this common problem that this patent seeks to correct.

DESCRIPTION OF THE BACKGROUND ART

FIG. 1 shows the round sheet of plastic with the three dimensional form. This form is designed to work with advanced equipment such as the BioStar or Drufamat. With even thickness and the arch partially formed, it allows less than half the distortion as flat sheets experience.

BRIEF SUMMARY OF THE INVENTION

Figure 1:
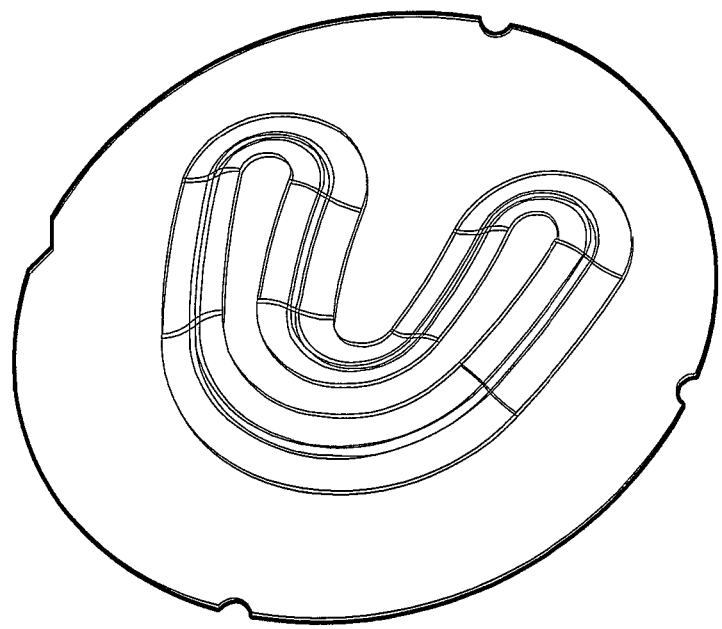
Figure 2:
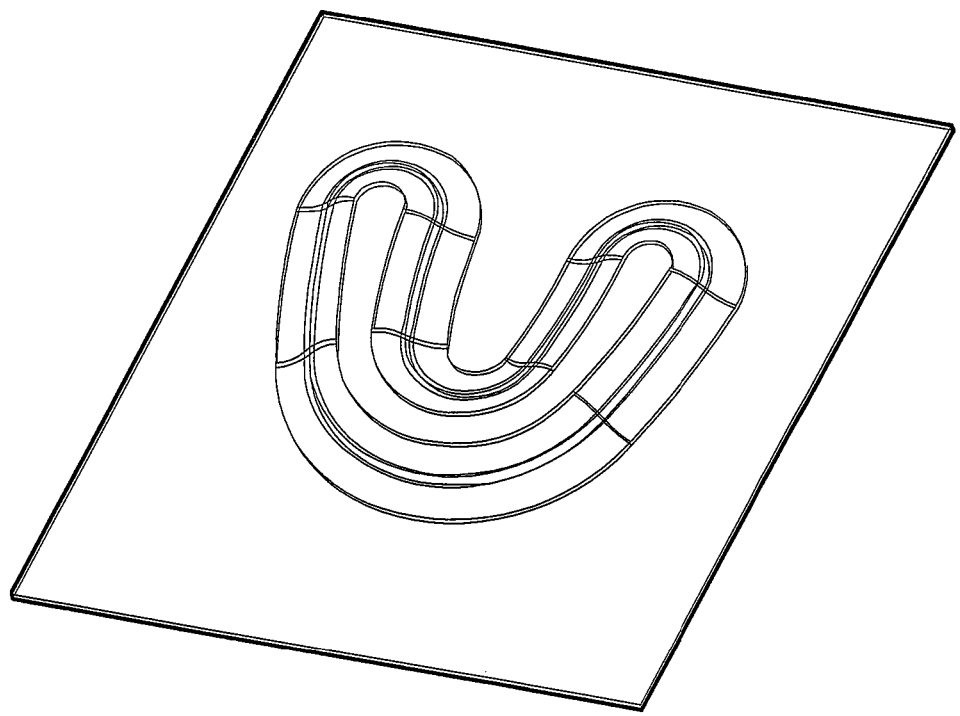
FIG. 2 shows the application in a square sheet configuration design to be used with the Raintree Essix manual system thermoformer. Again, the formed target area has uniform thickness while being in 3D.
Figure 3:
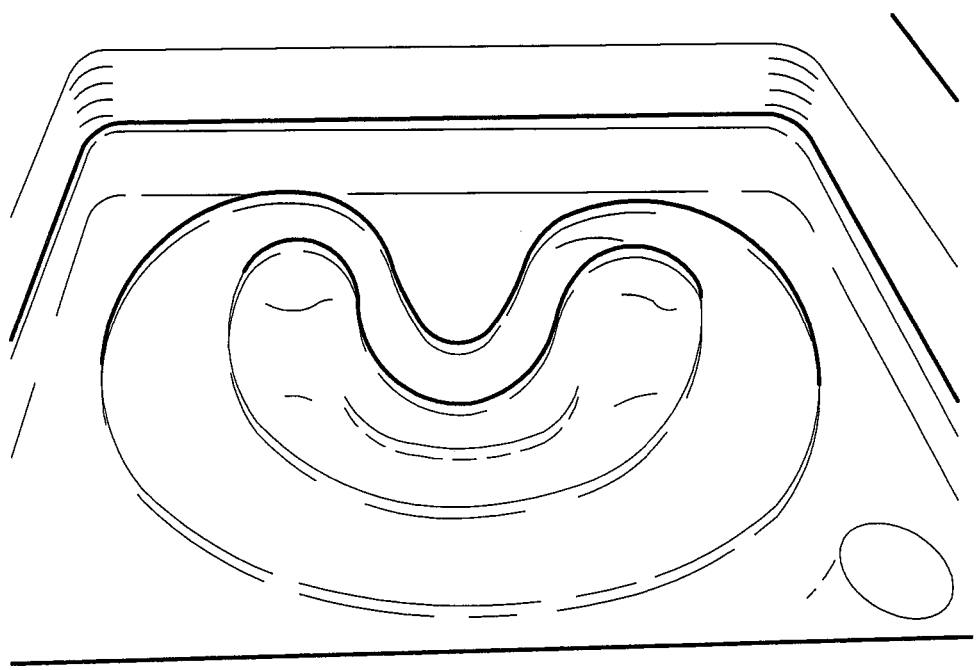
FIG. 3 shows the plastic as it heated to the desired temperature. Unlike current available plastic, it flattens rather than slumps greatly reducing the stretching experience with the current sheets available and increasing its wear toughness.
Figure 4:
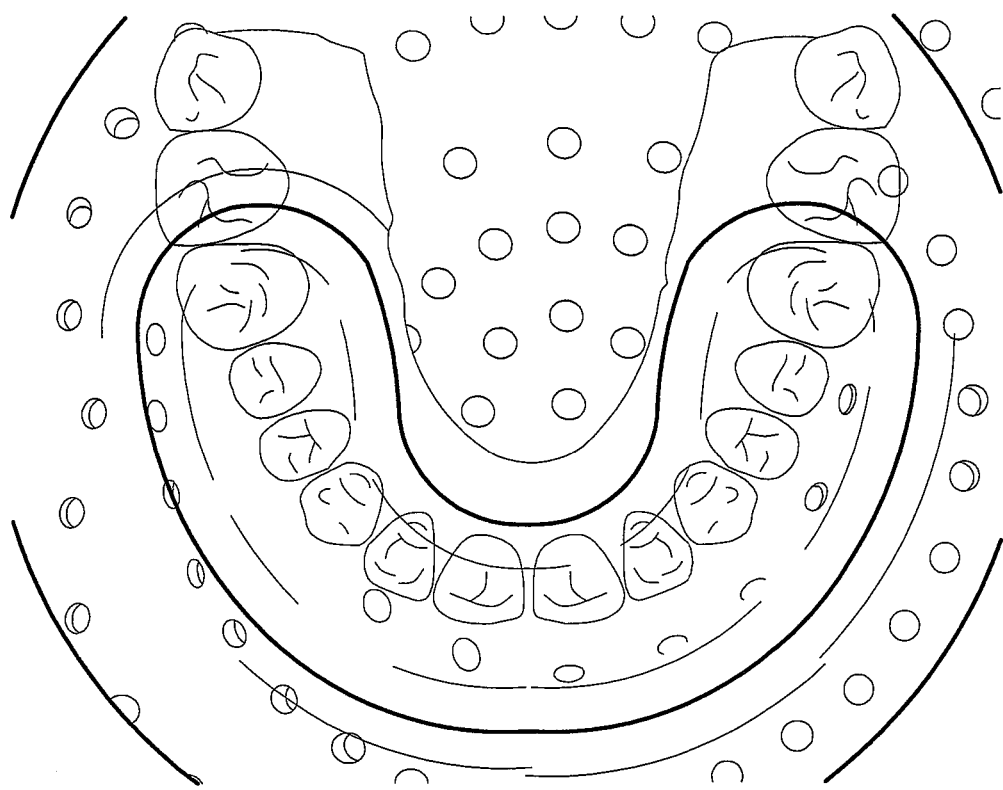
FIG. 4 shows the application with the application centered over the target mold for vacuum.
Figure 5:
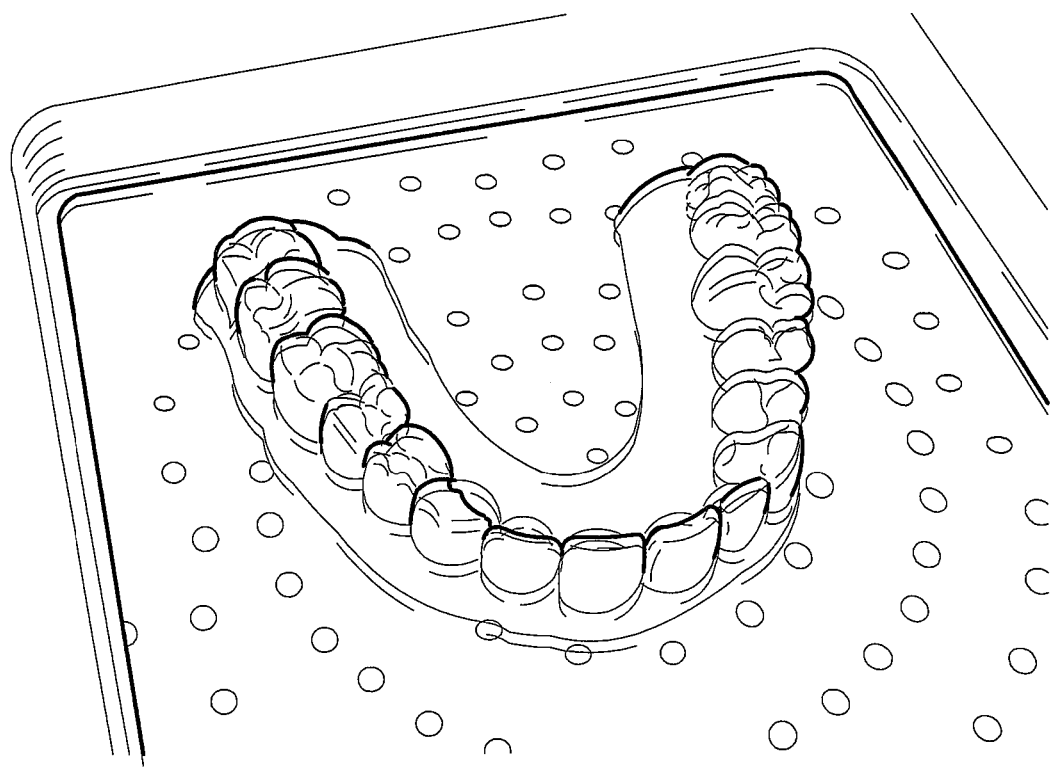
FIG. 5 shows a formed tray that can be made without chill spray, reducing the cost of fabrication.

Failed appliances have long annoyed doctors and patients and this patent proposes to eliminate most of it.

The narrow range of medical plastics eliminates use of some of the major "tough" plastics that have evolved. Rather, we propose to make the current medical grade plastics more acceptable.

This invention provides three solutions:
1. Varying the thickness in the area that is stretched over the model so that when it thins it becomes more uniform in thickness.
2. Making the plastic uniform in thickness but preforming a 3D area that partially builds in part of the area that would be stretched so that it thins much less than a flat sheet.
3. Doing both so that the average draw keeps the thickness after forming nearly uniform.

DETAILED DESCRIPTION OF THE INVENTION

It is known in the profession that there are two main plastics available that have good forming characteristics. One, polystyrene, has excellent clarity and stiffness but poor wear resistance. The other, polyvinylchloride (PVC) has much greater wear resistance but is cloudy after forming and less aesthetic. These are available from Raintree Essix of Metairie, La. and Great Lakes in Buffalo N.Y. These same companies also offer the main desktop thermoforming machines, the BioStar and the Raintree Essix. One is a digital solution and the other analog, respectively. The choice is made regarding the volume that is used.

The doctor takes an alginate impression of the patient's malocclusion. It then is filled with stone or plastic to make a positive model of the dentition. Depending on the thermoformer, a rectangular or round sheet of plastic, from 0.020" to 0.040" thick, is mounted in the chamber. The model is placed in the bed, the bottom of which is a vacuum chamber. At the top is a heating coil. When the machine has reached its ideal temperature, it heats the plastic until it slumps and then lays the slumped plastic over the model. The vacuum kicks on and pulls the plastic tight over the plaster model so it becomes a negative of the positive model. As discussed in USP (Dann patent) indicates a chill spray is used to quickly set the form so it doesn't begin to plastically deform during the cooling process.

The problem is that the plastic has deformed as much as 2" deep over the area where the model was, which is an area of about 7" by ¾". Since the plastic had a fixed thickness to start, it has thinned to as much as 50% its original thickness. Many have tried to solve this by going to the stronger PVC material but some patients are uncomfortable with its aesthetics and it doesn't have the spring of PS. Others have tried thicker original sheets but the thicker sheets lose the spring characteristic along the edges that help hold the plastic in the mouth. Also, it can be too thick in areas where there is less stretch, such as lower anteriors, and disrupt the bite, creating an overbite.

This application offers the following solutions:
This invention provides three solutions:
1. Varying the thickness in the area that is stretched over the model so that when it thins it becomes more uniform in thickness.
2. Making the plastic uniform in thickness but preforming a 3D area that partially builds in part of the area that would be stretched so that it thins much less than a flat sheet.
3. Doing both so that the average draw keeps the thickness after forming nearly uniform.

By varying the thickness to improve wear resistance; the plastic is extruded instead of rolled so that one can vary the thickness by area of the sheets. Extruding machines are known to be capable of working easily with Polystyrene plastics. The PVC would be unnecessary, as the higher translucency of Polystyrene would be most desired by the patient while the wear resistance would be ideal.

The next solution works for both plastics by creating as the sheet is extruded, a 3-D area about ½" to 1.5" that is preformed in the shape of a wide arch so that during forming, the plastic will be stretched less than 50%. This concept has been tested at Glenroe Technologies and they have found less than 25% loss of thickness. This means a thinner plastic can be used, creating less overbite at the end of treatment and less mid-treatment emergency visits when the tray fails.

Finally, using a combined extrusion and stamping process, the first two processes can be combined to produce an ideal sheet that is thicker in the area of 3D preforming. While this process will be more expensive, it allows greater security for the professional and the patient that treatment results will be realized without failure, even if just used as a retainer. Surveys show that 25% of retainers and all activators are made this way and it is estimated that 3 million are made each year worldwide.

It is already known that an arch is between 5.5 and 7" long, that it is no more than 1.5 cm deep, and the sheet sizes for the varied machines is well documented. It is then just a matter of creating the 3D sheets in the prescribed area of the sheet where the activation will typically occur. Testing has shown that rather than slumping, the plastic will flatten when ready and hit the model at its dictated thickness.

It is anticipated that due to cost, one version will solely have the 3D affect and the other the 3D and thickness affect. It is also anticipated that the cloudy PVC will be unnecessary although it will be made available.

Many doctors form several plastic appliances at the same time should there be a failure at the onset. In a sense, much of this is futile as if it is used as an active appliance, the teeth will have moved during the term. For retainers, this is okay but eliminating this duplication can save many millions of dollars in labor and plastic.

More importantly, makers of active appliances, such as Align Technologies InvisAlign, rely on the aligners to be durable enough to make it through the phase of treatment that they have programmed. If an aligner fails, then the patient must return to the doctor, who will have to take a progress impression and model, and it will have to be sent in for a mid course correction and reanalyzed by the computers in order to make a new complete set of trays. Although the doctor is insured to a limited amount of corrections, it takes a lot of time and can lead to longer treatment of the patient, many times months longer. The doctor and InvisAlign cannot increase their fees so it is a loss to them, and the patient will be frustrated with the relapse and increased treatment time.

This application is limit to discomfort of failed treatment, lower the cost to doctors and labs, and promote better results and prosperity for all involved.

What is claimed is:

1. A plastic dental sheet for thermoforming of dental devices comprising:
   a first area having a first thickness and;
   a second area thicker than the first area and comprising a general U-shape of a wide arch corresponding to at least a portion of a positive model of a dentition; and
   a continuous transition portion completely surrounded by the first area and tapering between from the second area to the first area and the second area; the transition portion comprising a continuous, generally U-shape comprising a shape of a wide arch corresponding to at least a portion of a positive model of a dentition, and, the continuous transition portion defining a ridge completely surrounding the second area, the sheet being thermoformable over the positive model to form a negative model of the dentition;
   wherein the second area and the continuous transition portion define a cavity shaped to receive at least a portion of the positive model of the dentition;
   wherein a varying thickness of the second area corresponds with the dentition where thinning occurs during thermoforming of the sheet; and
   wherein the second area is stretchable over at least a potion of the positive model.

2. The plastic dental sheet as in claim 1 comprising polystyrene.

3. The plastic dental sheet as in claim 1 wherein the negative model is more than 80% translucent after thermoforming.

4. The plastic dental sheet as in claim 1, wherein the second area is a polystyrene plastic that stretches less than 25%.

5. The plastic dental sheet as in claim 1, wherein the second area further comprises an area about ½" to 1.5" wide.

6. The plastic dental sheet as in claim 5, wherein the sheet is comprised of a thermoformable plastic that stretches to less than 25% of the sheet original thickness.

7. The plastic dental sheet as in claim 1, wherein the sheet is a round sheet.

8. The plastic dental sheet as in claim 1, wherein the sheet is a rectangular sheet.

9. The plastic dental sheet as in claim 1, wherein the sheet is formable without chill spray.

10. The plastic dental sheet as in claim 1, wherein the sheet is extrudable.

11. The plastic dental sheet as in claim 1, wherein the sheet is extrudable and capable of being stamped.

12. The plastic dental sheet as in claim 1, wherein the sheet flattens rather than slumps.

\* \* \* \* \*